(12) United States Patent
Matsuda

(10) Patent No.: US 9,105,441 B2
(45) Date of Patent: Aug. 11, 2015

(54) MOBILE X-RAY IMAGE CAPTURING APPARATUS

(71) Applicant: CANON KABUSHIKI KAISHA, Tokyo (JP)

(72) Inventor: Daizo Matsuda, Funabashi (JP)

(73) Assignee: Canon Kabushiki Kaisha, Tokyo (JP)

( * ) Notice: Subject to any disclaimer, the term of this patent is extended or adjusted under 35 U.S.C. 154(b) by 118 days.

(21) Appl. No.: 14/056,862

(22) Filed: Oct. 17, 2013

(65) Prior Publication Data
US 2014/0112455 A1   Apr. 24, 2014

(30) Foreign Application Priority Data

Oct. 19, 2012 (JP) ................................. 2012-232113

(51) Int. Cl.
*H05G 1/02* (2006.01)
*H01J 35/16* (2006.01)
*A61B 6/00* (2006.01)

(52) U.S. Cl.
CPC ............... *H01J 35/16* (2013.01); *A61B 6/4405* (2013.01); *A61B 6/56* (2013.01)

(58) Field of Classification Search
CPC ....... A61B 6/4405; A61B 6/4429; A61B 6/56
USPC ................................... 378/193–198
See application file for complete search history.

(56) References Cited

U.S. PATENT DOCUMENTS

2006/0120512 A1   6/2006  Watanabe
2008/0192899 A1   8/2008  Kump et al.

FOREIGN PATENT DOCUMENTS

| JP | 2006239070 A | 9/2006 |
| JP | 2009201561 A | 9/2009 |
| JP | 2010094162 A | 4/2010 |
| JP | 2010273827 A | 12/2010 |

*Primary Examiner* — Courtney Thomas
(74) *Attorney, Agent, or Firm* — Canon USA Inc. IP Division

(57) ABSTRACT

A mobile X-ray capturing apparatus includes an X-ray tube for irradiating an object with X ray, an arm for holding the X-ray tube, and a support pillar for holding the arm so as to facilitate arrangement of units. Further, the mobile X-ray capturing apparatus includes an arm energizing unit provided with an electrode incorporated in the arm for supplying power or a signal necessary for the X-ray tube, and a support pillar energizing unit provided with an electrode incorporated in the support pillar for supplying the power or the signal to the arm.

7 Claims, 9 Drawing Sheets

MOBILE X-RAY IMAGE CAPTURING APPARATUS

BACKGROUND OF THE INVENTION

1. Field of the Invention

The present invention relates to a mobile X-ray image capturing apparatus capable of moving on a floor surface in a hospital etc.

2. Description of the Related Art

A conventional mobile X-ray image capturing apparatus having a mobile function is formed with a control device mobile cart for controlling a length of an arm and a support pillar supporting the mobile X-ray capturing apparatus, and incorporates a high voltage power source device for supplying power to the X-ray capturing apparatus in the cart.

Further, the X-ray capturing apparatus incorporates a control device for controlling the length of the arm and the support pillar supporting the mobile X-ray capturing apparatus, a control device for controlling a mobile mechanism of the mobile cart, and a battery device for supplying the power to an entire mobile X-ray image capturing apparatus. An alternating high-voltage cable is provided between the high-voltage power source device in the mobile cart and an X-ray tube.

At a lower portion of the mobile cart, wheels for moving the X-ray capturing apparatus and casters capable of changing an apparatus direction are provided. At an upper portion of the mobile cart, a support pillar is vertically disposed, and one side of the arm is held by the support pillar with a fixing tool. Furthermore, the arm is provided with the X-ray tube for generating X ray.

The mobile cart is equipped with the casters and driving wheels to move the mobile cart. An operator holds a grasp portion to move the mobile cart. Japanese Patent Application Laid-Open No. 2010-94162 discusses the mobile X-ray image capturing apparatus according to the conventional technique.

When X-ray capturing is performed in a general hospital room, the mobile X-ray image capturing apparatus is typically used. Japanese Patent Application Laid-Open No. 2010-94162 discusses the mobile X-ray image capturing apparatus including a conventional X-ray tube (not illustrated), which is provided with the alternating high-voltage cable and a control cable between the high-voltage power source device and the X-ray tube.

To reduce drop of the voltage in the high-voltage cable appearing from the high-voltage power source device to the X-ray tube, an area of a conductive member needs to be increased to lower resistance. Under such a situation, the high-voltage cable having the increased area of the conductive member may disturb arrangement of each portion of the apparatus.

SUMMARY OF THE INVENTION

The present invention is directed to facilitate arrangement of each portion in a mobile X-ray image capturing apparatus.

A mobile X-ray capturing apparatus includes an X-ray tube for irradiating a object with X ray, an arm for holding the X-ray tube, and a support pillar for holding the arm. Further, the mobile X-ray capturing apparatus includes an arm energizing unit provided with an electrode incorporated in the arm for supplying power or a signal necessary for the X-ray tube, and a support pillar energizing unit provided with an electrode incorporated in the support pillar for supplying the power or the signal to the arm.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DETAILED DESCRIPTION OF THE EMBODIMENTS

Various exemplary embodiments, features, and aspects of the invention will be described in detail below with reference to the drawings. It should be noted that the relative arrangement of the components, the numerical expressions and numerical values set forth in these embodiments do not limit the scope of the present invention unless it is specifically stated otherwise.

Figure 1:
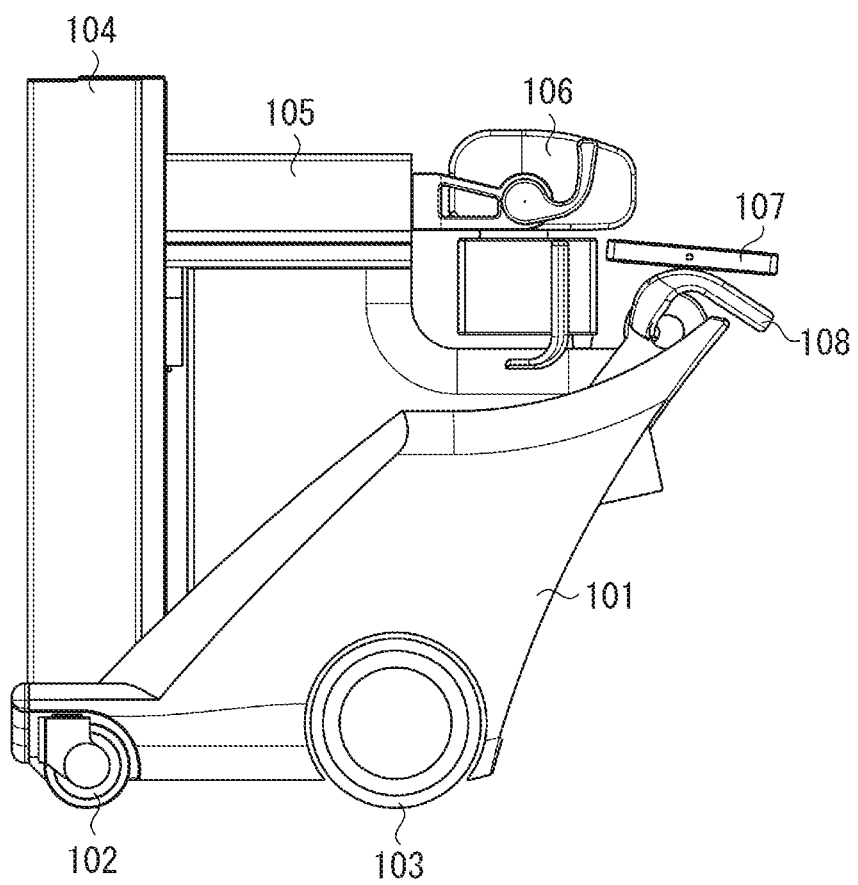
FIG. 1 illustrates a mobile X-ray image capturing apparatus.

FIG. 1 illustrates a mobile X-ray image capturing apparatus according to the present exemplary embodiment. The mobile X-ray image capturing apparatus is generally referred to as an X-ray visiting car, and mounted with a buttery for operating each constituent member inside. The battery is a main power source for operating each constituent member and should have a great capacity. As illustrated in a diagram, the mobile X-ray image capturing apparatus includes the X-ray tube for emitting the X ray, an arm for holding the X-ray tube, a support pillar for supporting the arm, and a main body apparatus.

The arm and the support pillar according to the exemplary embodiment are each formed of a plurality of steps that are connected with each other, thereby capable of being elongated, shortened, and rotated. Further, an X-ray sensor (not illustrated) detects the X ray transmitted through a object to perform an X-ray picture taking to capture the X-ray image.

The mobile X-ray image capturing apparatus includes a mobile cart energizing unit 101 for distributing necessary power from the battery to operate a driving wheel 103 for moving the mobile X-ray image capturing apparatus. A housing of the mobile cart energizing unit 101 is disposed with a front wheel 102 and the driving wheel 103. The front wheel 102 and the driving wheel 103 support weight of the mobile X-ray image capturing apparatus and move it.

The mobile X-ray image capturing apparatus includes a support pillar energizing unit 104 that is disposed inside the support pillar of the mobile X-ray image capturing apparatus and energize the necessary power from the battery. The support pillar is rotatable and, even when the support pillar is rotated, the support pillar energizing unit 104 can be energized.

The mobile X-ray image capturing apparatus is disposed inside the arm of the mobile X-ray image capturing apparatus and includes the arm energizing unit 105 for energizing the necessary power from the battery. The arm can be elongated and shortened, and even when the arm is elongated or shortened, the arm energizing unit 105 can be energized.

The mobile X-ray image capturing apparatus includes an X-ray tube 106 for emitting the X ray. The X-ray tube 106 is held by the arm, and by elongating or shortening of the arm and rotating of the support pillar, it can be moved to an arbitrary position.

The mobile X-ray image capturing apparatus includes a display unit 107 for displaying an X-ray image acquired by taking the X-ray picture of an object with the mobile X-ray image capturing apparatus according to the present exemplary embodiment. The display unit 107 displays a control graphical user interface (GUI) for operating each constituent member of the mobile X-ray image capturing apparatus, in addition to the captured X-ray images.

The mobile X-ray image capturing apparatus includes an operation unit 108 for operating each constituent member of the mobile X-ray image capturing apparatus according to the present exemplary embodiment. The operation unit 108 includes an operation unit such as a general keyboard and mouse.

Figure 2:
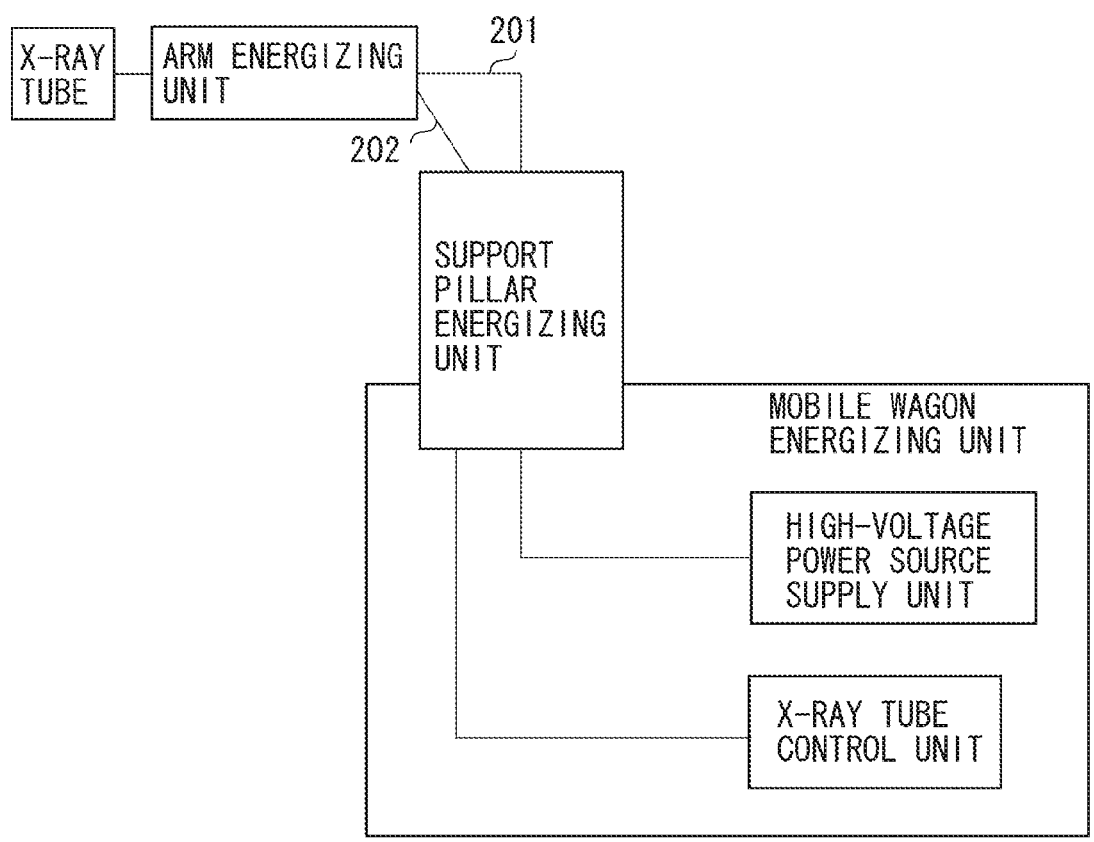
FIG. 2 illustrates wiring connection among power and control signals of the mobile X-ray image capturing apparatus.

FIG. 2 illustrates wiring connection of the power and the control signals of the mobile X-ray image capturing apparatus according to the present exemplary embodiment. The mobile X-ray image capturing apparatus includes a power-source line 201 for energizing the power and a control line 202 for transmitting/receiving the control signal.

The support pillar energizing unit 104 is connected to the power-source supply unit and the X-ray tube control unit. The power supplied from the power source supply unit such as a battery and an inverter is supplied to the X-ray tube via the support pillar energizing unit 104 and the arm energizing unit 105. The control signal for controlling the X-ray tube is transmitted by the X-ray tube control unit to the X-ray tube via the support pillar energizing unit 104 and the arm energizing unit 105.

Figure 3:
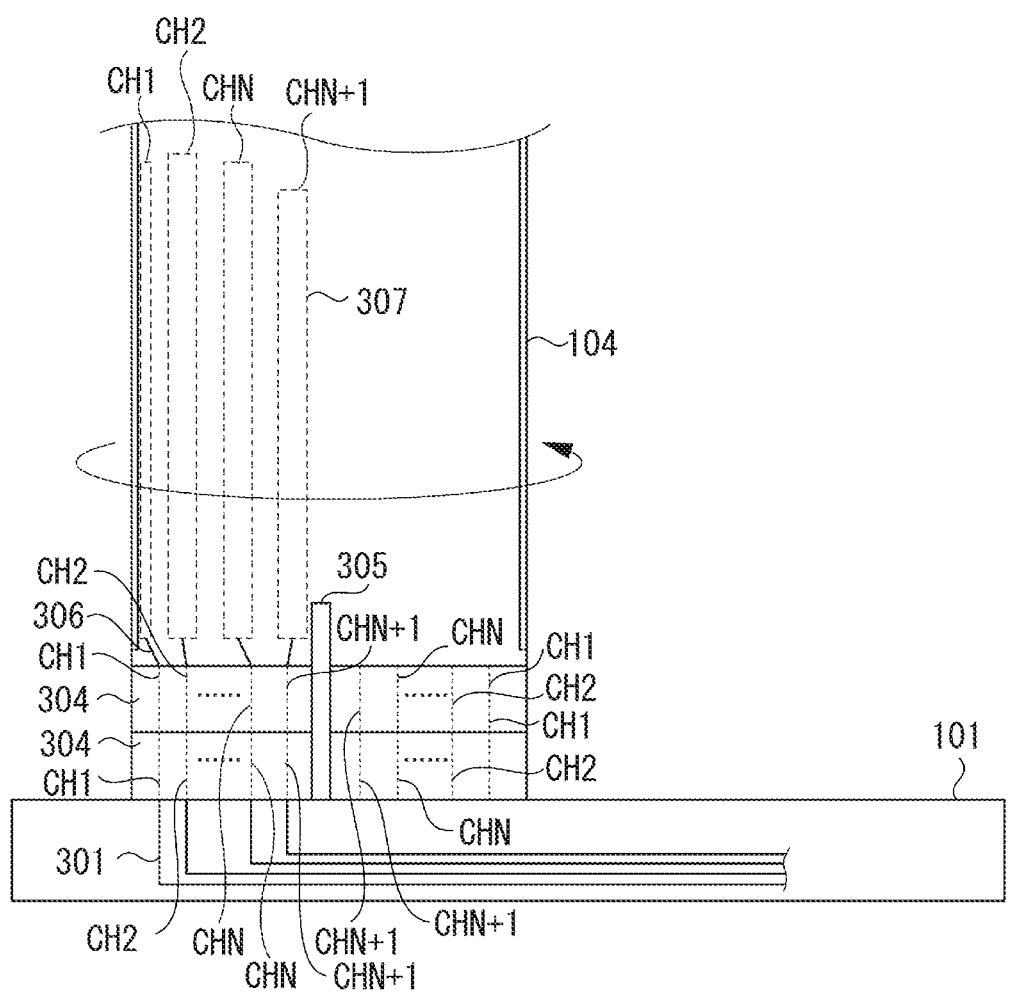
FIG. 3 illustrates an internal mechanism of a mobile cart energizing unit and a support pillar energizing unit.

FIG. 3 illustrates an internal mechanism of the mobile cart energizing unit 101 and the support pillar energizing unit 104.

The mobile cart energizing unit 101 supplies the power from the power-source supply unit via a cart internal cable 301, and transmits the control signal from the X-ray tube control unit. The cart internal cable 301 is connected to a rotating electrode on the cart side.

The support pillar incorporates a support pillar internal electrode 307 for distributing the power or the control signal. In other words, the mobile X-ray capturing apparatus includes the X-ray tube 106 for irradiating the object with the X ray, the arm for holding the X-ray tube 106, and the support pillar for holding the arm. Further, the mobile X-ray capturing apparatus includes the arm energizing unit 105 provided with an electrode incorporated in the arm for supplying power or the signal necessary for the X-ray tube, and the support pillar energizing unit 104 provided with an electrode incorporated in the support pillar for supplying the power or the signal to the arm.

Figure 4:
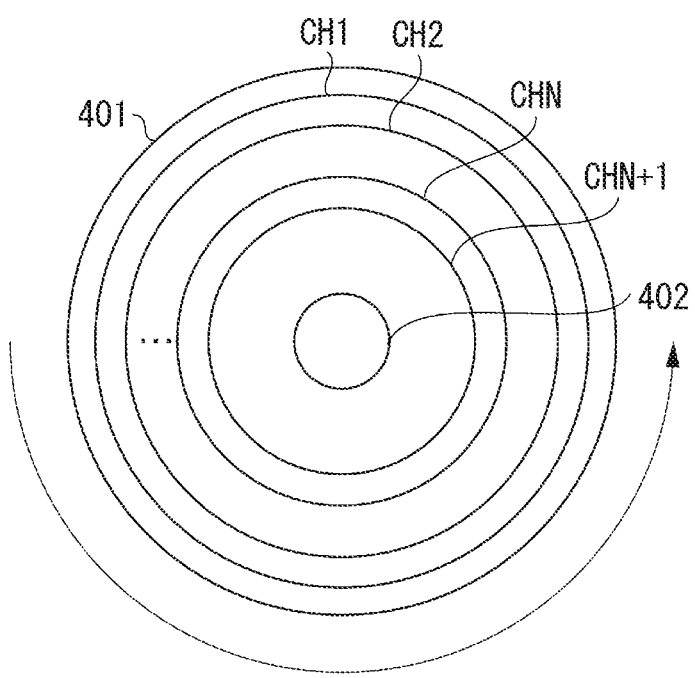
FIG. 4 illustrates a cross-sectional view of a mechanism of rotating electrodes on a cart side and a support pillar side.

FIG. 4 illustrates a cross-sectional view of the mechanism of the rotating electrode on the cart side and a rotating electrode on the support pillar side. The rotating electrode on the cart side is provided with a rotation axis 305 for rotating the support pillar energizing unit with respect to the cart energizing unit. In a periphery of the rotation axis 305, a rotating electrode 304 is provided, and is connected to the cart internal cable 301.

The rotating electrode 304 includes the electrodes from CH1 to CH N+1. The electrodes of the power-source line 201 and the control line 202 are allocated to the above electrodes. Since the rotating electrode is formed in a concentric circle, by increasing a length and width of a circumference, the area of the conductor can be increased to reduce the resistance thereof to be lower than that of the cable.

The rotating electrode on the cart side and the rotating electrode on the support pillar side having the same configuration are overlaid with each other. The rotating electrodes 304 can come into contact with each other by using, for example, an energizing electrode brush, and thus can be rotated. The rotating electrode 304 is connected to the support pillar internal electrode 307 via the support pillar relay cable 306 to energize it.

The support pillar internal electrode 307 is provided on an inner surface of the housing of the support pillar energizing unit 104, and painted with material having good conductivity such as metal coating. CH1 to CH N+1 of the support pillar internal electrodes 307 are each connected to the rotating electrode 304 at the cart side. By increasing the width and thickness of the conductor, the area thereof can be increased to reduce the resistance thereof to be lower than that of an external cable.

With this arrangement, while energizing the power-source line 201 and the control line 202, the arm energizing unit 105 can be rotated with respect to the mobile cart energizing unit 101.

Figure 5:
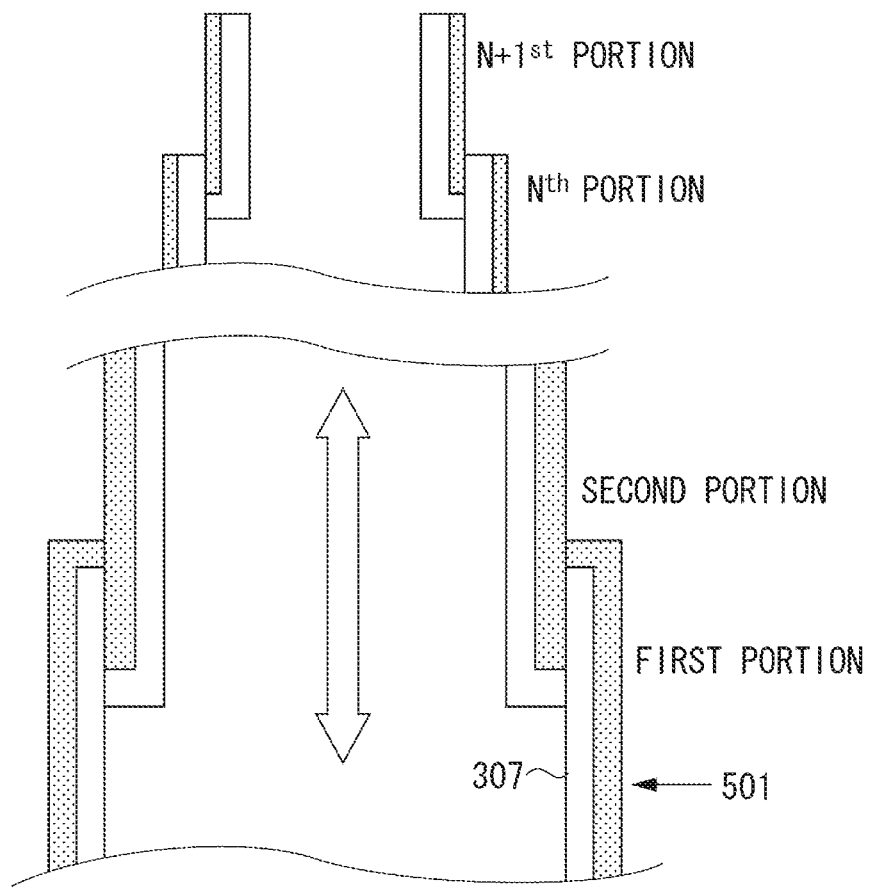
FIG. 5 illustrates an internal configuration of the support pillar energizing unit.

FIG. 5 illustrates an internal configuration of the support pillar energizing unit 104. Inside the support pillar energizing unit 104, a support pillar energizing element 501 having a first step to an N+1$^{st}$ step is provided. The support pillar energizing element 501 and the support pillar internal electrode 307 are in contact with each other via the electrode such as the electrode brush and are energized.

The first step to the N+1$^{st}$ step of the support pillar internal electrodes 307 are energized with each other, and thus can be moved in an arrow direction. With this arrangement, in the support pillar energizing unit 104, while the power-source line 201 and the control line 202 are energized, the support pillar energizing element 501 can be operated vertically.

Figure 6:
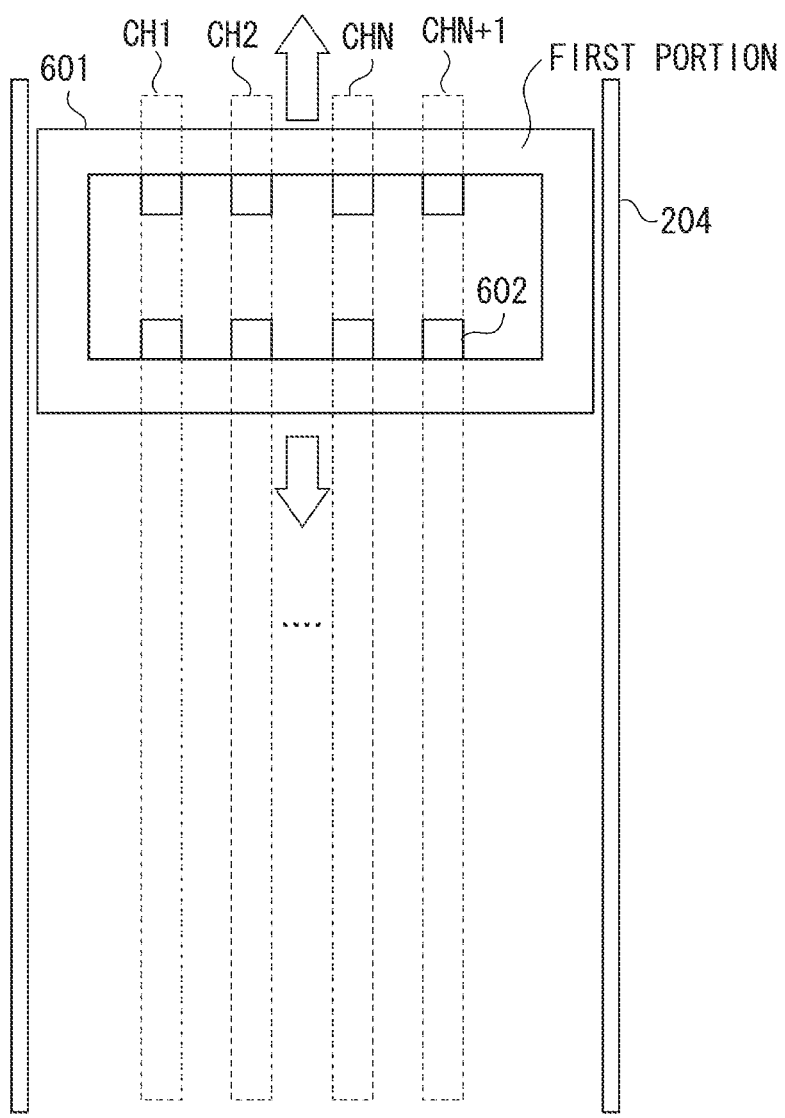
FIG. 6 illustrates a connection portion between the support pillar energizing unit and the arm energizing unit.

FIG. 6 illustrates the connection portion between the support pillar energizing unit 104 and the arm energizing unit 105, showing the electrodes for supplying the power and transmitting the control signal among the units. In the support pillar energizing unit 104, the support pillar internal electrode 307 is provided with an arm energizing element 601 of the first step of the arm energizing unit 105.

Figure 7:
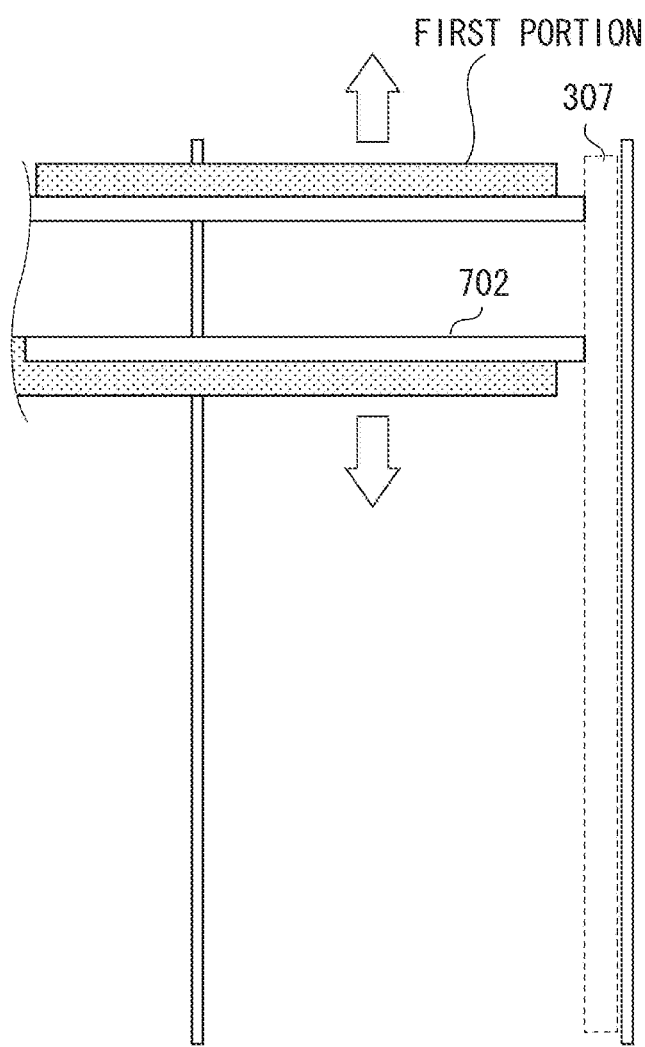
FIG. 7 is aside face view illustrating the connection portion illustrated in FIG. 6.

The arm energizing element 601 is in contact with each of CH1 to CH N+1 of an arm internal electrode 602 via the electrode such as the electrode brush. FIG. 7 is a side face view of FIG. 6. While an arm internal electrode 702 and the support pillar internal electrode 307 are in contact with each other to be energized, the arm energizing unit 105 can be vertically moved. With this arrangement, while the power-source line 201 and the control line 202 are energized, the arm energizing unit 105 can be vertically operated with respect to the support pillar energizing unit 104.

Figure 8:
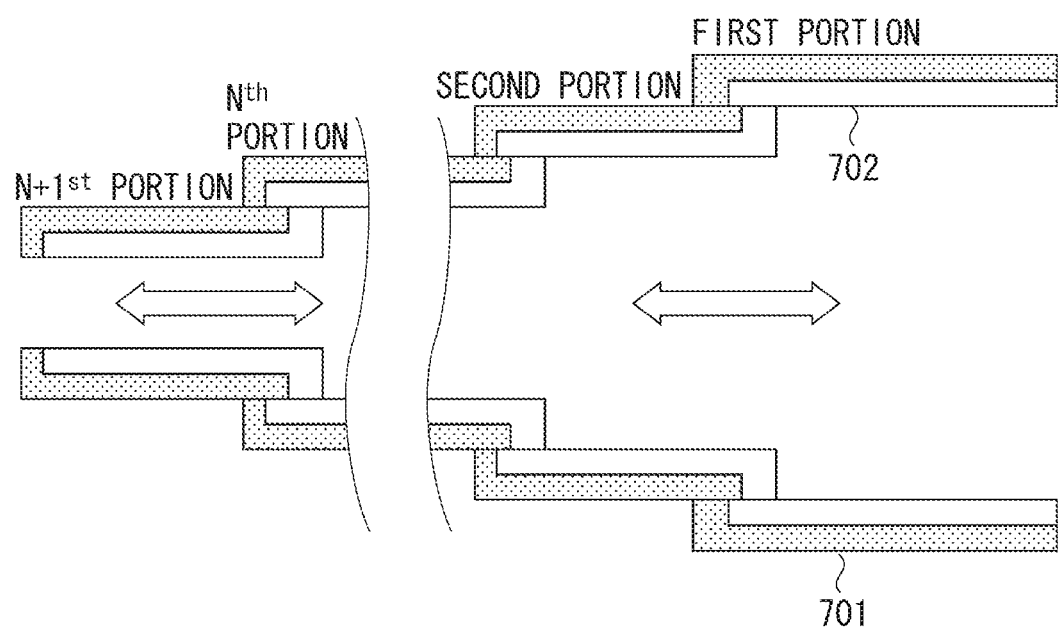
FIG. 8 illustrates a configuration of the arm energizing unit.

FIG. 8 illustrates a configuration of the arm energizing unit 105, which includes the arm energizing element 701 having the first step to the N+1$^{st}$ step. Each arm energizing elements 701 include the arm internal electrode 702. The arm energizing elements 701 are energized with the arm internal electrodes 702 that are in contact with each other, and energized via the electrode such as the electrode brush.

The arm internal electrode 702 is energized from the first step to the N+1$^{st}$ step, and the arm energizing unit 105 can be moved in the arrow direction. With this arrangement, in the arm energizing unit 105, while the power-source line 201 and the control line 202 are energized, the arm energizing element 701 can be elongated or shortened.

Figure 9:
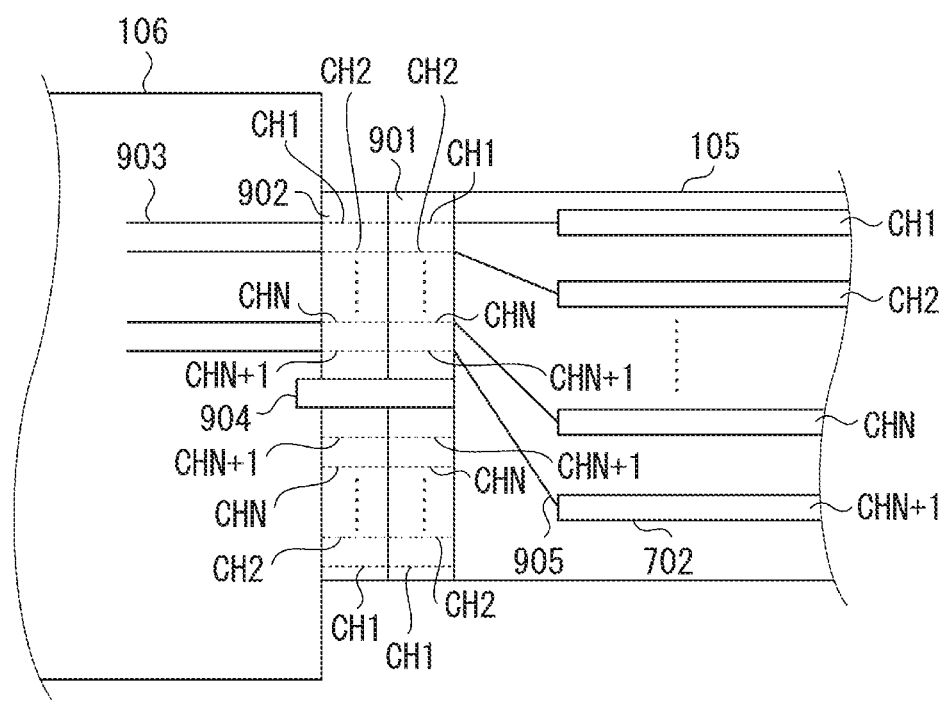
FIG. 9 illustrates a connection portion between the arm energizing unit and the X-ray tube.

FIG. 9 illustrates a connection portion between the arm energizing unit 105 and the X-ray tube 106, which includes the arm internal electrodes 702 from CH1 to CH N+1. The power-source line 201 and the control line 202 are allocated to the arm internal electrodes 702, and the power is distributed to an X-ray tube internal cable 903 disposed inside the X-ray tube 106 via an arm side rotating electrode 901 and an X-ray tube side rotating electrode 902.

The arm side rotating electrode 901 and the X-ray tube side rotating electrode 902 are configured in a similar mechanism to that of the rotating electrode on the cart side and the support pillar side rotating electrode. The rotating electrodes can be rotated in contact with each other via the electrode such as the electrode brush and energized. With this arrangement, while the power-source line 201 and the control line 202 are energized, the X-ray tube 106 can be rotated with respect to the arm energizing unit 105.

According to the present exemplary embodiment, even without the external cable, by the X-ray tube 106, the arm energizing unit 105, the support pillar energizing unit 104, and the mobile cart energizing unit 101, the power-source line 201 and the control line 202 can be energized to facilitate arrangement of each unit. Further, by increasing the area of the conductor in the housing of each unit, a voltage drop can be suppressed.

As illustrated in FIGS. 1 to 9, according to the present exemplary embodiment, in order to energize the rotating electrode on the cart side, the support pillar side rotating electrode, the support pillar internal electrode 307, the arm internal electrode 602, the arm side rotating electrode 901, and the X-ray tube side rotating electrode 902, the electrode brush is described as an example. However, wireless communication and wireless power supply may also be employed.

Other Embodiments

Aspects of the present invention can also be realized by a computer of a system or apparatus (or devices such as a CPU or MPU) that reads out and executes a program recorded on a memory device to perform the functions of the above-described embodiment (s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable storage medium).

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2012-232113 filed Oct. 19, 2012, which is hereby incorporated by reference herein in its entirety.

What is claimed is:

1. A mobile X-ray-capturing apparatus comprising:
   an X-ray tube for irradiating an object with X-rays;
   an arm for holding the X-ray tube;
   a support pillar for holding the arm;
   a first electrical conductor comprising an electrode incorporated in the arm for supplying power or a signal to the X-ray tube; and
   a second electrical conductor comprising an electrode incorporated in the support pillar for supplying power or the signal to the arm.

2. The mobile X-ray-capturing apparatus according to claim 1,
   wherein the arm comprises a plurality of connected portions; and
   wherein the first electrical conductor is configured to supply power or a signal to the plurality of arm portions.

3. The mobile X-ray-capturing apparatus according to claim 1, wherein the first electrical conductor is configured to receive a wireless power or signal transmission.

4. The mobile X-ray-capturing apparatus according to claim 1,
   wherein the support pillar comprises a plurality of connected portions; and
   wherein the second electrical conductor is configured to supply power or a signal to the plurality of support pillar portions.

5. The mobile X-ray-capturing apparatus according to claim 1, wherein the second electrical conductor is configured to receive a wireless power or signal transmission.

6. The mobile X-ray-capturing apparatus according to claim 1, wherein the support pillar is configured to be rotatable with respect to the mobile X-ray capturing apparatus.

7. The mobile X-ray capturing apparatus according to claim 1,
   further comprising a mobile cart containing a power source and a third electrical conductor, the third electrical conductor being rotatably connected to the second electrical conductor, and being configured to supply the power or the signal to the second electrical conductor either directly or by performing wireless transmission of power or the signal.

* * * * *